US005750388A

United States Patent [19]
Berka et al.

[11] Patent Number: 5,750,388
[45] Date of Patent: May 12, 1998

[54] PURIFIED SCYTALIDIUM LACCASES AND NUCLEIC ACIDS ENCODING SAME

[75] Inventors: Randy Michael Berka; Sheryl Ann Thompson, both of Davis; Feng Xu, Woodland, all of Calif.

[73] Assignee: Novo Nordish Bio Tech, Inc, Davis, Calif.

[21] Appl. No.: 749,882

[22] Filed: Nov. 15, 1996

Related U.S. Application Data

[63] Continuation of Ser. No. 253,784, Jun. 3, 1994, abandoned.
[51] Int. Cl.⁶ ............................................. C12N 9/02
[52] U.S. Cl. ................ 435/189; 435/252.3; 435/252.33; 435/254.1; 435/254.3; 435/320.1; 536/23.1; 536/23.2
[58] Field of Search .............................. 435/189, 252.3, 435/252.33, 254.1, 254.3, 320.1; 536/23.1, 23.2

[56] References Cited

PUBLICATIONS

Berka et al., Abstracts of Papers, BIOT 196, vol. 209, No. 1-2, 1995.

Germann et al., The Journal of Biological Chemistry, vol. 263, No. 2, pp. 885-896, 1988.

Perry, C.R. et al. *J. Gen. Microbiol.* 139:1209-1218 (1993).

Schilling, B. et al. *Curr. Genet.* 22:197-203 (1992).

*Primary Examiner*—Robert A. Wax
*Assistant Examiner*—Nashaat T. Nashed
*Attorney, Agent, or Firm*—Steve T. Zelsen, Esq; Elias J. Lambiris, Esq

[57] ABSTRACT

The present invention relates to isolated nucleic acid constructs containing a sequence encoding a Scytalidium laccase, and the laccase proteins encoded thereby.

23 Claims, 12 Drawing Sheets

```
1    CTGAATTTAAATACAGGAAGATCGCATTCAATCCAGCCTAGACTGCACAATGGTTCTGCA                        60

61   CGACCGTCGCACACCTGCCAATAGTGTTAATAACGGCCTAATACC ATG AAG CGC TT                       116
                                                   M   K   R   F

117  C TTC ATT AAT AGC CTT CTG CTT CTC GCA GGG CTC CTC AAC TCA GG                      161
       F   I   N   S   L   L   L   L   A   G   L   L   N   S   G

162  G GCC CTC GCG GCT CCG TCT ACA CAT CCC AGA TCA AAC CCC GAC AT                      206
       A   L   A   A   P   S   T   H   P   R   S   N   P   D   I

207  A CTG CTT GAA AGA GAT GAC CAC TCC CTT ACG TCT CGG CAA GGT AG                      251
       L   L   E   R   D   D   H   S   L   T   S   R   Q   G   S

252  C TGT CAT TCT CCA AGC AAC CGC GCC TGT TGG TGC TCT GGC TTC GA                      296
       C   H   S   P   S   N   R   A   C   W   C   S   G   F   D

297  T ATC AAC ACG GAT TAT GAG ACC AAG ACT CCA AAC ACC GGA GTG GT                      341
       I   N   T   D   Y   E   T   K   T   P   N   T   G   V   V

342  G CGG GTTAGTATCCCAAGTTACGTTTGACCAAGAAATGGACGTGAAGTGTGCTG                          398
       R   R

399  ACTCTCCCGCTAG TAC ACC TTT GAT ATC ACC GAA GTC GAC AAC CGC CC                      446
                   Y   T   F   D   I   T   E   V   D   N   R   P
```

Fig. 1A

```
447  C GGT CCC GAT GGG GTC ATC AAG GAG AAG CTC ATG CTT ATC AAC GA    491
       G   P   D   G   V   I   K   E   K   L   M   L   I   N   D

492  C AAA CTC CTG G GTAGGGTCCTCTCGAACGCCTGCTGCCACACAGCGTAAAACT      547
       K   L   L

548  AACGAACCGCTAG GC CCG ACA GTC TTC GCA AAC TGG GGC GAC ACC ATC    595
                      G   P   T   V   F   A   N   W   G   D   T   I

596  GAG GTG ACC GTC AAC CAC CTG AGA ACC AAC GG GTAAGCGTTCGGA        643
       E   V   T   V   N   H   L   R   T   N   G

644  CACAAAGCCCAGCAACCTAGACACACTCAACTGACCAAGTAG A ACC TCC ATC CAC    698
                                                  T   S   I   H

699  TGG CAC GGC TTG CAC CAA AAA GGA ACC AAC TAC CAC GAC GGC GCC    743
       W   H   G   L   H   Q   K   G   T   N   Y   H   D   G   A

744  AAC GGC GTG ACC GAG TGT CCC ATC CCG CCC GGT GGC TCC CGA GTC    788
       N   G   V   T   E   C   P   I   P   P   G   G   S   R   V

789  TAC AGC TTC CGA GCG CGC CAA TAT GGA ACG TCA TGG TAC CAC TCC    833
       Y   S   F   R   A   R   Q   Y   G   T   S   W   Y   H   S
```

Fig. 1B

| Pos | | | | | | | | | | | | | | | Pos |
|---|---|---|---|---|---|---|---|---|---|---|---|---|---|---|---|
| 834 | CAC H | TTC F | TCC S | GCC A | CAG Q | TAT Y | GGC G | AAC N | GGC G | GTG V | AGC S | GGC G | GCC A | ATC I | CAG Q | 878 |
| 879 | ATC I | AAC N | GGA G | CCC P | GCC A | TCC S | CTG L | CCC P | TAC Y | GAC D | ATC I | GAC D | CTC L | GGC G | GTC V | 923 |
| 924 | CTC L | CCG P | CTG L | CAG Q | GAC D | TGG W | TAC Y | TAC Y | AAG K | TCC S | GCC A | GAC D | CAG Q | CTC L | GTC V | 968 |
| 969 | ATC I | GAG E | ACC T | CTG L | GCC A | AAG K | GGC G | AAC N | GCT A | CCG P | TTC F | AGC S | GAC D | AAC N | GTG V | 1013 |
| 1014 | CTC L | ATC I | AAC N | GGC G | ACC T | GCA A | AAG K | CAC H | CCC P | ACC T | GGC G | ACT T | GGC G | GAA E | GGG G | 1058 |
| 1059 | TAC Y | GCC A | ATC I | GTG V | AAG K | CTC L | ACC T | CCC P | GGC G | AAA K | CGC R | CAT H | CGC R | CTG L | CGG R | 1103 |
| 1104 | CTC L | ATC I | AAC N | ATG M | TCG S | GTG V | GAG E | AAC N | CAC H | TTC F | CAG Q | GTC V | TCG S | CTG L | GCG A | 1148 |
| 1149 | AAG K | CAC H | ACC T | ATG M | ACG T | ATC I | GCG A | GCG A | GAC D | ATG M | GTC V | CCC P | GTC V | GCG A | AAC N | 1193 |

Fig. 1C

| | | | | | | | | | | | | | | |
|---|---|---|---|---|---|---|---|---|---|---|---|---|---|---|
| 1194 | GCC A | ATG M | ACC T | GTC V | GAC D | AGC S | CTG L | TTT F | ATG M | GCC A | GTC V | GGG G | CAG Q | CGG R | TAT Y | 1238 |
| 1239 | GAT D | GTT V | ACC T | ATC I | GAC D | GCG A | AGC S | CAG Q | GCG A | GTG V | GGG G | TAC Y | AAT N | TGG W | TTC F | 1283 |
| 1284 | AAC N | ATC I | ACC T | TTT F | GGA G | CAG Q | CAG Q | AAG K | TGC C | GGC G | TTC F | TCG S | CAC H | AAT N | 1328 |
| 1329 | CCG P | GCG A | GCA A | GCC A | ATC I | TTT F | CGC R | TAC Y | GAG E | TGC C | GGC G | CCT P | GCT A | GAC D | 1373 |
| 1374 | CTG L | CCG P | ACG T | GAT D | CCT P | GGC G | GCT A | CCA P | AAG K | CAT H | CAG Q | TGC C | CTG L | 1418 |
| 1419 | GAC D | ACT T | TTG L | GAT D | CTT L | TCA S | CCG P | GTG V | GTG V | CAA Q | AAC N | GTG V | CCG P | GTT V | 1463 |
| 1464 | GAC D | GGG G | TTC F | GTC V | AAA K | GAG E | CCT P | GCG A | AAT N | ACG T | CTG L | CCG P | GTG V | ACG T | CTC L | 1508 |
| 1509 | CAT H | GTT V | GAC D | CAG Q | GCC A | GCG A | GCT A | CCA P | CAC H | GTG V | TTT F | ACG T | TGG W | AAG K | ATC I | 1553 |

```
1554 AAC GGG AGC GCT GCG GAC GTG GAC TGG GAC AGG CCG GTG CTG GAG  1598
      N   G   S   A   A   D   V   D   W   D   R   P   V   L   E

1599 TAT GTC ATG AAC AAT GAC CTG TCT AGC ATT CCG GTC AAG AAC AAC  1643
      Y   V   M   N   N   D   L   S   S   I   P   V   K   N   N

1644 ATT GTG AGG GTG GAC GGA GTC AAC GAG TGG ACG TAC TGG CTC GTC  1688
      I   V   R   V   D   G   V   N   E   W   T   Y   W   L   V

1689 GAA AAC GAC CCG GAG CGC CTC AGT TTG CCG CAT CCG ATG CAT      1733
      E   N   D   P   E   R   L   S   L   P   H   P   M   H

1734 CTA CAC GTAAGTCACATCCCCCACTACCATTCGGAATGACCACCAGGTACTGACACC 1790
      L   H

1791 CTCCTCCTCAATAG GGA CAC GAT TTC TTT GTC CTA GGC CGC TCC CCC G 1838
                    G   H   D   F   F   V   L   G   R   S   P

1839 AC GTC TCG CCC GAT TCA GAA ACC CGC TTC GTC TTT GAC CCG GCC G 1883
      D   V   S   P   D   S   E   T   R   F   V   F   D   P   A

1884 TC GAC CTC CCC CGT CTG CGC GGA CAC AAC CCC GTC CGG CGC GAC G 1928
      V   D   L   P   R   L   R   G   H   N   P   V   R   R   D
```

```
1929  TC ACC ATG CTT CCC GCG CGC GGC TGG CTG CTG CTG GCC TTC CGC A  1973
         V  T   M   L   P   A   R   G   W   L   L   L   A   F   R

1974  CG GAC AAC CCG GGC GCG TGG GCG GCG TTG TTC CAC TGC CAC ATC GCG TGG C  2018
         T  D   N   P   G   A   W   A   A   L   F   H   C   H   I   A   W

2019  AC GTG TCG GGC TTA AGC GTC GAC TTT CTG GAG CGG CCG GAC G  2063
         H  V   S   G   L   S   V   D   F   L   E   R   P   D

2064  AG CTG CGC GGG CAG CTG ACG GGA GAG AGC AAG GCG GAG TTG GAG C  2108
         E  L   R   G   Q   L   T   G   E   S   K   A   E   L   E

2109  GT GTT TGT CGC GAG TGG AAG GAT TGG GAG GCG AAG AGC CCG CAT G  2153
         R  V   C   R   E   W   K   D   W   E   A   K   S   P   H

2154  GG AAG ATC GAT TCG GGG TTG AAG CAG CGG CGA TGG GAT GCG TGA G  2198
         G  K   I   D   S   G   L   K   Q   R   R   W   D   A   *

2199  GTAGTTGGGCGGATTGTTTAACACGTAGTGGGTAAGGTTGGGGCGGGTTTGTTTGGCGTT  2258
```

Fig. 1F

2259 TTCAGGGGTTGGGGTGCGGATGCTGGTCATCCGGGAAACGGCTCTACAACTGGTGTCAAT 2318

2319 AGACTAATATAGAGTGATCAAAGAACTGAGGTTCTGAAAGAGGCCGTGGAAGTCGCGTTGT 2378

2379 GACTCCCTTTGCCATGTTGGGAAGTGTGGCTCAACATTGTGTTCAGGTTTGCTCAGGGTG 2438

2439 ATNTCGAACTGACGTNTTGATGAGGGTTATTGCNTAGA 2476

Fig. 1G

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 2476 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Scytalidium thermophilum ( i x ) FEATURE:
        ( A ) NAME/KEY: intron
        ( B ) LOCATION: 349..411

( i x ) FEATURE:
        ( A ) NAME/KEY: intron
        ( B ) LOCATION: 502..559

( i x ) FEATURE:
        ( A ) NAME/KEY: intron
        ( B ) LOCATION: 632..686

( i x ) FEATURE:
        ( A ) NAME/KEY: intron
        ( B ) LOCATION: 1739..1804

( i x ) FEATURE:
        ( A ) NAME/KEY: CDS
        ( B ) LOCATION: join (106..348, 412..501, 560..631, 687..1738, 1805..2194)

( x i ) SEQUENCE DESCRIPTION: SEQ ID NO: 1:

```
CTGAATTTAA ATACAGGAAG ATCGCATTCA ATCCAGCCTA GACTGCACAA TGGTTCTGCA         60

CGACCGTCGC ACACCTGCCA ATAGTGTTAA TAACGGCCTA ATACC ATG AAG CGC TTC        117
                                                  Met Lys Arg Phe
                                                   1

TTC ATT AAT AGC CTT CTG CTT CTC GCA GGG CTC CTC AAC TCA GGG GCC          165
Phe Ile Asn Ser Leu Leu Leu Leu Ala Gly Leu Leu Asn Ser Gly Ala
  5              10                  15                  20

CTC GCG GCT CCG TCT ACA CAT CCC AGA TCA AAC CCC GAC ATA CTG CTT          213
Leu Ala Ala Pro Ser Thr His Pro Arg Ser Asn Pro Asp Ile Leu Leu
             25                  30                  35

GAA AGA GAT GAC CAC TCC CTT ACG TCT CGG CAA GGT AGC TGT CAT TCT          261
Glu Arg Asp Asp His Ser Leu Thr Ser Arg Gln Gly Ser Cys His Ser
             40                  45                  50

CCA AGC AAC CGC GCC TGT TGG TGC TCT GGC TTC GAT ATC AAC ACG GAT          309
Pro Ser Asn Arg Ala Cys Trp Cys Ser Gly Phe Asp Ile Asn Thr Asp
         55                  60                  65

TAT GAG ACC AAG ACT CCA AAC ACC GGA GTG GTG CGG CGG GTTAGTATCC           358
```

```
                Tyr Glu Thr Lys Thr Pro Asn Thr Gly Val Val Arg Arg
                     70                  75              80

CAAGTTACGT TGACCAAGA AATGGACGTG AAGTGTGCTG ACTCTCCCGC TAG                    411

TAC ACC TTT GAT ATC ACC GAA GTC GAC AAC CGC CCC GGT CCC GAT GGG             459
Tyr Thr Phe Asp Ile Thr Glu Val Asp Asn Arg Pro Gly Pro Asp Gly
             85                  90                  95

GTC ATC AAG GAG AAG CTC ATG CTT ATC AAC GAC AAA CTC CTG GTAGG               506
Val Ile Lys Glu Lys Leu Met Leu Ile Asn Asp Lys Leu Leu
        100                 105                 110

GTCCTCTCGA ACGCCTGCGT CTGCCACACA GCGTAAAACT AACGAACCGC TAG                   559

GGC CCG ACA GTC TTC GCA AAC TGG GGC GAC ACC ATC GAG GTG ACC GTC             607
Gly Pro Thr Val Phe Ala Asn Trp Gly Asp Thr Ile Glu Val Thr Val
             115                 120                 125

AAC AAC CAC CTG AGA ACC AAC GGA GTAAGCGTTC GGACACAAAG CCCAGCAACC            661
Asn Asn His Leu Arg Thr Asn Gly
        130             135

TAGACACACT CAACTGACCA AGTAG ACC TCC ATC CAC TGG CAC GGC TTG CAC CAA         716
                            Thr Ser Ile His Trp His Gly Leu His Gln
                                        140                     145

AAA GGA ACC AAC TAC CAC GAC GGC GCC AAC GGC GTG ACC GAG TGT CCC             764
Lys Gly Thr Asn Tyr His Asp Gly Ala Asn Gly Val Thr Glu Cys Pro
                150                 155                 160

ATC CCG CCC GGT GGC TCC CGA GTC TAC AGC TTC CGA GCG CGC CAA TAT             812
Ile Pro Pro Gly Gly Ser Arg Val Tyr Ser Phe Arg Ala Arg Gln Tyr
            165                 170                 175

GGA ACG TCA TGG TAC CAC TCC CAC TTC TCC GCC CAG TAT GGC AAC GGC             860
Gly Thr Ser Trp Tyr His Ser His Phe Ser Ala Gln Tyr Gly Asn Gly
            180                 185                 190

GTG AGC GGC GCC ATC CAG ATC AAC GGA CCC GCC TCC CTG CCC TAC GAC             908
Val Ser Gly Ala Ile Gln Ile Asn Gly Pro Ala Ser Leu Pro Tyr Asp
    195                 200                 205

ATC GAC CTC GGC GTC CTC CCG CTG CAG GAC TGG TAC TAC AAG TCC GCC             956
Ile Asp Leu Gly Val Leu Pro Leu Gln Asp Trp Tyr Tyr Lys Ser Ala
210                 215                 220                 225

GAC CAG CTC GTC ATC GAG ACC CTG GCC AAG GGC AAC GCT CCG TTC AGC            1004
Asp Gln Leu Val Ile Glu Thr Leu Ala Lys Gly Asn Ala Pro Phe Ser
                230                 235                 240

GAC AAC GTC CTC ATC AAC GGC ACC GCA AAG CAC CCC ACC ACT GGC GAA            1052
Asp Asn Val Leu Ile Asn Gly Thr Ala Lys His Pro Thr Thr Gly Glu
            245                 250                 255

GGG GAG TAC GCC ATC GTG AAG CTC ACC CCG GGC AAA CGC CAT CGC CTG            1100
Gly Glu Tyr Ala Ile Val Lys Leu Thr Pro Asp Lys Arg His Arg Leu
        260                 265                 270

CGG CTC ATC AAC ATG TCG GTG GAG AAC CAC TTC CAG GTC TCG CTG GCG            1148
Arg Leu Ile Asn Met Ser Val Glu Asn His Phe Gln Val Ser Leu Ala
    275                 280                 285

AAG CAC ACC ATG ACG GTC ATC GCG GCG GAC ATG GTC CCC GTC AAC GCC            1196
Lys His Thr Met Thr Val Ile Ala Ala Asp Met Val Pro Val Asn Ala
290                 295                 300                 305

ATG ACC GTC GAC AGC CTG TTT ATG GCC GTC GGG CAG CGG TAT GAT GTT            1244
Met Thr Val Asp Ser Leu Phe Met Ala Val Gly Gln Arg Tyr Asp Val
                310                 315                 320

ACC ATC GAC GCG AGC CAG GCG GTG GGG AAT TAC TGG TTC AAC ATC ACC            1292
Thr Ile Asp Ala Ser Gln Ala Val Gly Asn Tyr Trp Phe Asn Ile Thr
            325                 330                 335

TTT GGA GGG CAG CAG AAG TGC GGC TTC TCG CAC AAT CCG GCG CCG GCA            1340
Phe Gly Gly Gln Gln Lys Cys Gly Phe Ser His Asn Pro Ala Pro Ala
        340                 345                 350

GCC ATC TTT CGC TAC GAG GGC GCT CCT GAC GCT CTG CCG ACG GAT CCT            1388
```

|     |     |     |     |     |     |     |     |     |     |     |     |     |     |     |     |
|-----|-----|-----|-----|-----|-----|-----|-----|-----|-----|-----|-----|-----|-----|-----|-----|
| Ala | Ile | Phe | Arg | Tyr | Glu | Gly | Ala | Pro | Asp | Ala | Leu | Pro | Thr | Asp | Pro |
| 355 |     |     |     |     | 360 |     |     |     |     | 365 |     |     |     |     |     |

```
GGC GCT GCG CCA AAG GAT CAT CAG TGC CTG GAC ACT TTG GAT CTT TCA     1436
Gly Ala Ala Pro Lys Asp His Gln Cys Leu Asp Thr Leu Asp Leu Ser
370             375                 380                  385

CCG GTG GTG CAA AAG AAC GTG CCG GTT GAC GGG TTC GTC AAA GAG CCT     1484
Pro Val Val Gln Lys Asn Val Pro Val Asp Gly Phe Val Lys Glu Pro
                390                 395                  400

GGC AAT ACG CTG CCG GTG ACG CTC CAT GTT GAC CAG GCC GCG GCT CCA     1532
Gly Asn Thr Leu Pro Val Thr Leu His Val Asp Gln Ala Ala Ala Pro
            405                 410                  415

CAC GTG TTT ACG TGG AAG ATC AAC GGG AGC GCT GCG GAC GTG GAC TGG     1580
His Val Phe Thr Trp Lys Ile Asn Gly Ser Ala Ala Asp Val Asp Trp
        420                 425                  430

GAC AGG CCG GTG CTG GAG TAT GTC ATG AAC AAT GAC CTG TCT AGC ATT     1628
Asp Arg Pro Val Leu Glu Tyr Val Met Asn Asn Asp Leu Ser Ser Ile
    435                 440                  445

CCG GTC AAG AAC AAC ATT GTG AGG GTG GAC GGA GTC AAC GAG TGG ACG     1676
Pro Val Lys Asn Asn Ile Val Arg Val Asp Gly Val Asn Glu Trp Thr
450                 455                  460                  465

TAC TGG CTC GTC GAA AAC GAC CCG GAG GGC CGC CTC AGT TTG CCG CAT     1724
Tyr Trp Leu Val Glu Asn Asp Pro Glu Gly Arg Leu Ser Leu Pro His
                470                 475                  470

CCG ATG CAT CTA CAC GTAAGTCACA TCCCCCACTA CCATTCGGAA TGACCACCAG     1779
Pro Met His Leu His
            475

GTACTGACAC CCTCCTCCTC AATAG GGA CAC GAT TTC TTT GTC CTA GGC CGC     1831
                            Gly His Asp Phe Phe Val Leu Gly Arg
                                        480                  485

TCC CCC GAC GTC TCG CCC GAT TCA GAA ACC CGC TTC GTC TTT GAC CCG     1879
Ser Pro Asp Val Ser Pro Asp Ser Glu Thr Arg Phe Val Phe Asp Pro
            490                 495                  500

GCC GTC GAC CTC CCC CGT CTG CGC GGA CAC AAC CCC GTC CGG CGC GAC     1927
Ala Val Asp Leu Pro Arg Leu Arg Gly His Asn Pro Val Arg Arg Asp
            505                 510                  515

GTC ACC ATG CTT CCC GCG CGC GGC TGG CTG CTG CTG GCC TTC CGC ACG     1975
Val Thr Met Leu Pro Ala Arg Gly Trp Leu Leu Leu Ala Phe Arg Thr
        520                 525                  530

GAC AAC CCG GGC GCG TGG TTG TTC CAC TGC CAC ATC GCG TGR CAC GTG     2023
Asp Asn Pro Gly Ala Trp Leu Phe His Cys His Ile Ala Trp His Val
535                 540                  545

TCG GGC GGG TTA AGC GTC GAC TTT CTG GAG CGG CCG GAC GAG CTG CGC     2071
Ser Gly Gly Leu Ser Val Asp Phe Leu Glu Arg Pro Asp Glu Leu Arg
550                 555                  560                  565

GGG CAG CTG ACG GGA GAG AGC AAG GCG GAG TTG GAG CGT GTT TGT CGC     2119
Gly Gln Leu Thr Gly Glu Ser Lys Ala Glu Leu Glu Arg Val Cys Arg
                570                 575                  580

GAG TGG AAG GAT TGG GAG GCG AAG AGC CCG CAT GGG AAG ATC GAT TCG     2167
Glu Trp Lys Asp Trp Glu Ala Lys Ser Pro His Gly Lys Ile Asp Ser
            585                 590                  595

GGG TTG AAG CAG CGG CGA TGG GAT GCG TGAGGTAGTT GGGCGGATTG           2214
Gly Leu Lys Gln Arg Arg Trp Asp Ala
            600                 605

TTTAACACGT AGTGGGTAAG GTTGGGGCGG GTTTGTTTGG CGTTTTCAGG GGTTGGGGTG   2274

CGGATGCTGG TCATCCGGGA AACGGCTCTA CAACTGGTGT CAATAGACTA ATATAGAGTG   2334

ATCAAAGAAC TGAGGTTCTG AAAGAGGCGT GGAAGTCGCG TTGTGACTCC CTTTGCCATG   2394

TTGGGAAGTG TGGCTCAACA TTGTGTTCAG GTTTGCTCAG GGTGATNTCG AACTGACGTN   2454

TTGATGAGGG TTATTGCNTA GA                                           2476
```

( 2 ) INFORMATION FOR SEQ ID NO: 2:

( i ) SEQUENCE CHARACTERISTICS:
        ( A ) LENGTH: 616 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Scytalidium thermophilum ( x i ) SEQUENCE DESCRIPTION: SEQ ID NO: 2:

```
Met Lys Arg Phe Phe Ile Asn Ser Leu Leu Leu Ala Gly Leu Leu
 1               5                  10                  15

Asn Ser Gly Ala Leu Ala Ala Pro Ser Thr His Pro Arg Ser Asn Pro
            20                  25                  30

Asp Ile Leu Leu Glu Arg Asp Asp His Ser Leu Thr Ser Arg Gln Gly
            35                  40                  45

Ser Cys His Ser Pro Ser Asn Arg Ala Cys Trp Cys Ser Gly Phe Asp
 50                  55                  60

Ile Asn Thr Asp Tyr Glu Thr Lys Thr Pro Asn Thr Gly Val Val Arg
 65                  70                  75                  80

Arg Tyr Thr Phe Asp Ile Thr Glu Val Asp Asn Arg Pro Gly Pro Asp
                85                  90                  95

Gly Val Ile Lys Glu Lys Leu Met Leu Ile Asn Asp Lys Leu Leu Gly
                100                 105                 110

Pro Thr Val Phe Ala Asn Trp Gly Asp Thr Ile Glu Val Thr Val Asn
                115                 120                 125

Asn His Leu Arg Thr Asn Gly Thr Ser Ile His Trp His Gly Leu His
    130                 135                 140

Gln Lys Gly Thr Asn Tyr His Asp Gly Ala Asn Gly Val Thr Glu Cys
145                 150                 155                 160

Pro Ile Pro Pro Gly Gly Ser Arg Val Tyr Ser Phe Arg Ala Arg Gln
                165                 170                 175

Tyr Gly Thr Ser Trp Tyr His Ser His Phe Ser Ala Gln Tyr Gly Asn
                180                 185                 190

Gly Val Ser Gly Ala Ile Gln Ile Asn Gly Pro Ala Ser Leu Pro Tyr
                195                 200                 205

Asp Ile Asp Leu Gly Val Leu Pro Leu Gln Asp Trp Tyr Tyr Lys Ser
    210                 215                 220

Ala Asp Gln Leu Val Ile Glu Thr Leu Ala Lys Gly Asn Ala Pro Phe
225                 230                 235                 240

Ser Asp Asn Val Leu Ile Asn Gly Thr Ala Lys His Pro Thr Thr Gly
                245                 250                 255

Glu Gly Glu Tyr Ala Ile Val Lys Leu Thr Pro Asp Lys Arg His Arg
                260                 265                 270

Leu Arg Leu Ile Asn Met Ser Val Glu Asn His Phe Gln Val Ser Leu
                275                 280                 285

Ala Lys His Thr Met Thr Val Ile Ala Ala Asp Met Val Pro Val Asn
    290                 295                 300

Ala Met Thr Val Asp Ser Leu Phe Met Ala Val Gly Gln Arg Tyr Asp
305                 310                 315                 320

Val Thr Ile Asp Ala Ser Gln Ala Val Gly Asn Tyr Trp Phe Asn Ile
                325                 330                 335
```

-continued

| | | | | | | | | | | | | | | |
|---|---|---|---|---|---|---|---|---|---|---|---|---|---|---|
|Thr|Phe|Gly|Gly 340|Gln|Gln|Lys|Cys|Gly 345|Phe|Ser|His|Asn|Pro 350|Ala|Pro|
|Ala|Ala|Ile 355|Phe|Arg|Tyr|Glu|Gly 360|Ala|Pro|Asp|Ala|Leu 365|Pro|Thr|Asp|
|Pro|Gly 370|Ala|Ala|Pro|Lys|Asp 375|His|Gln|Cys|Leu|Asp 380|Thr|Leu|Asp|Leu|
|Ser 385|Pro|Val|Val|Gln|Lys 390|Asn|Val|Pro|Val|Asp 395|Gly|Phe|Val|Lys|Glu 400|
|Pro|Gly|Asn|Thr|Leu 405|Pro|Val|Thr|Leu|His 410|Val|Asp|Gln|Ala|Ala 415|Ala|
|Pro|His|Val|Phe 420|Thr|Trp|Lys|Ile|Asn 425|Gly|Ser|Ala|Ala|Asp 430|Val|Asp|
|Trp|Asp|Arg 435|Pro|Val|Leu|Glu|Tyr 440|Val|Met|Asn|Asn|Asp 445|Leu|Ser|Ser|
|Ile|Pro 450|Val|Lys|Asn|Asn|Ile 455|Val|Arg|Val|Asp|Gly 460|Val|Asn|Glu|Trp|
|Thr 465|Tyr|Trp|Leu|Val|Glu 470|Asn|Asp|Pro|Glu|Gly 475|Arg|Leu|Ser|Leu|Pro 480|
|His|Pro|Met|His 485|Leu|His|Gly|His|Asp|Phe 490|Phe|Val|Leu|Gly|Arg 495|Ser|
|Pro|Asp|Val|Ser 500|Pro|Asp|Ser|Glu|Thr 505|Arg|Phe|Val|Phe|Asp 510|Pro|Ala|
|Val|Asp|Leu 515|Pro|Arg|Leu|Arg|Gly 520|His|Asn|Pro|Val|Arg 525|Arg|Asp|Val|
|Thr|Met 530|Leu|Pro|Ala|Arg|Gly 535|Trp|Leu|Leu|Leu|Ala 540|Phe|Arg|Thr|Asp|
|Asn 545|Pro|Gly|Ala|Trp|Leu 550|Phe|His|Cys|His|Ile 555|Ala|Trp|His|Val|Ser 560|
|Gly|Gly|Leu|Ser|Val 565|Asp|Phe|Leu|Glu|Arg 570|Pro|Asp|Glu|Leu|Arg 575|Gly|
|Gln|Leu|Thr|Gly 580|Glu|Ser|Lys|Ala|Glu 585|Leu|Glu|Arg|Val|Cys 590|Arg|Glu|
|Trp|Lys|Asp 595|Trp|Glu|Ala|Lys|Ser 600|Pro|His|Gly|Lys|Ile 605|Asp|Ser|Gly|
|Leu|Lys 610|Gln|Arg|Arg|Trp|Asp 615|Ala| | | | | | | | |

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CGAGACTGAT AACTGGCTTG G        21

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

ACGGCGCATT GTCAGGGAAG T        21

( 2 ) INFORMATION FOR SEQ ID NO:5:

( i ) SEQUENCE CHARACTERISTICS:
       ( A ) LENGTH: 5 amino acids
       ( B ) TYPE: amino acid
       ( C ) STRANDEDNESS: single
       ( D ) TOPOLOGY: linear ( x i ) SEQUENCE DESCRIPTION: SEQ ID NO:5:

Asp Ser Gly Leu Lys
 1               5

( 2 ) INFORMATION FOR SEQ ID NO:6:

( i ) SEQUENCE CHARACTERISTICS:
       ( A ) LENGTH: 65 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:6:

TCGAGATGAA GCGCTTCTTC ATTAATAGCC TTCTGCTTCT CGCAGGGCTC CTCAACTCAG    60

GGGCC    65

( 2 ) INFORMATION FOR SEQ ID NO:7:

( i ) SEQUENCE CHARACTERISTICS:
       ( A ) LENGTH: 57 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:7:

CCTGAGTTGA GGAGCCCTGC GAGAAGCAGA AGGCTATTAA TGAAGAAGCG CTTCATC    57

( 2 ) INFORMATION FOR SEQ ID NO:8:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:8:

GTCATGAACA ATGACCT    17

( 2 ) INFORMATION FOR SEQ ID NO:9:

( i ) SEQUENCE CHARACTERISTICS:
       ( A ) LENGTH: 33 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:9:

AGAGAGTCTA GATTAAACAA TCCGCCCAAC TAC    33

PURIFIED SCYTALIDIUM LACCASES AND NUCLEIC ACIDS ENCODING SAME

This application is a continuation of Ser. No. 08/253,784, filed Jun. 3, 1994, now abandoned.

FIELD OF THE INVENTION

The present invention relates to isolated nucleic acid fragments encoding a fungal oxidoreductase enzyme and the purified enzymes produced thereby. More particularly, the invention relates to nucleic acid fragments encoding a phenol oxidase, specifically a laccase, of a thermophilic fungus, Scytalidium.

BACKGROUND OF THE INVENTION

Laccases (benzenediol:oxygen oxidoreductases) are multi-copper containing enzymes that catalyze the oxidation of phenolics. Laccase-mediated oxidations result in the production of aryloxy-radical intermediates from suitable phenolic substrate; the ultimate coupling of the intermediates so produced provides a combination of dimeric, oligomeric, and polymeric reaction products. Such reactions are important in nature in biosynthetic pathways which lead to the formation of melanin, alkaloids, toxins, lignins, and humic acids. Laccases are produced by a wide variety of fungi, including ascomycetes such as Aspergillus, Neurospora, and Podospora, the deuteromycete Botrytis, and basidiomycetes such as Collybia, Fomes, Lentinus, Pleurotus, Trametes, and perfect forms of Rhizoctonia. Laccase exhibits a wide range of substrate specificity, and each different fungal laccase usually differs only quantitatively from others in its ability to oxidize phenolic substrates. Because of the substrate diversity, laccases generally have found many potential industrial applications. Among these are lignin modification, paper strengthening, dye transfer inhibition in detergents, phenol polymerization, juice manufacture, phenol resin production, and waste water treatment.

Although the catalytic capabilities are similar, laccases made by different fungal species do have different temperature and pH optima, and these may also differ depending on the specific substrate. A number of these fungal laccases have been isolated, and the genes for several of these have been cloned. For example, Choi et al. (Mol. Plant-Microbe Interactions 5: 119–128, 1992) describe the molecular characterization and cloning of the gene encoding the laccase of the chestnut blight fungus, Cryphonectria parasitica. Kojima et al. (J. Biol. Chem. 265: 15224–15230, 1990; JP 2-238885) provide a description of two allelic forms of the laccase of the white-rot basidiomycete Coriolus hirsutus. Germann and Lerch (Experientia 41: 801, 1985; PNAS USA 83: 8854–8858, 1986) have reported the cloning and partial sequencing of the Neurospora crassa laccase gene. Saloheimo et al. (J. Gen. Microbiol. 137: 1537–1544, 1985; WO 92/01046) have disclosed a structural analysis of the laccase gene from the fungus Phlebia radiata.

Attempts to express laccase genes in heterologous fungal systems frequently give very low yields(Kojima et al., supra; Saloheimo et al., Bio/Technol. 9: 987–990, 1991). For example, heterologous expression of Phlebia radiata laccase in Trichoderma reesei gave only 20 mg per liter of active enzyme(Saloheimo, 1991, supra). Although laccases have great commercial potential, the ability to express the enzyme in significant quantities is critical to their commercial utility. At the present time there are no laccases which are expressed at high levels in commercially utilized hosts such as Aspergillus. Thus, the need exists for a laccase which can be produced in commercially useful (i.e., gram per liter or more) quantities. The present invention fulfills such a need.

SUMMARY OF THE INVENTION

The present invention relates to a DNA construct containing a nucleic acid sequence encoding a Scytalidium laccase. The invention also relates to an isolated laccase encoded by the nucleic acid sequence. Preferably, the laccase is substantially pure. By "substantially pure" is meant a laccase which is essentially (i.e., ≧90%) free of other non-laccase proteins.

In order to facilitate production of the novel laccase, the invention also provides vectors and host cells comprising the claimed nucleic acid fragment, which vectors and host cells are useful in recombinant production of the laccase. The nucleic acid fragment is operably linked to transcription and translation signals capable of directing expression of the laccase protein in the host cell of choice. A preferred host cell is a fungal cell, most preferably of the genus Aspergillus. Recombinant production of the laccase of the invention is achieved by culturing a host cell transformed or transfected with the nucleic acid fragment of the invention, or progeny thereof, under conditions suitable for expression of the laccase protein, and recovering the laccase protein from the culture.

The laccases of the present invention are useful in a number of industrial processes in which oxidation of phenolics is required. These processes include lignin manipulation, juice manufacture, phenol polymerization and phenol resin production.

BRIEF DESCRIPTION OF THE FIGURES

FIG. 1 illustrates the nucleotide(SEQ ID NO: 1) and amino acid (SEQ ID NO: 2) sequence of Scytalidium thermophila laccase. Letters without corresponding amino acids in the nucleotide sequence indicate the position of introns.

DETAILED DESCRIPTION OF THE INVENTION

Scytalidium thermophilum is a thermophilic deuteromycete, and a member of the Torula-Humicola complex which are recognized as dominant species in mushroom compost. Other members of the complex include Humicola grisea Traaen var. thermoidea Cooney & Emerson, H. insolens Cooney & Emerson, and Torula thermophila Cooney & Emerson, the latter of which has been reassigned to Scytalidium thermophilum by Austwick (N.Z. J. Agric. Res. 19: 25–33, 1976). Straatsma and Samson (Mycol. Res. 97: 321–328, 1993) have recently determined that both H. grisea var. thermoides and H. insolens should be considered as examples of the species *Scytalidium thermophilum* as well. *S. indonesiacum* (Hedger et al., Trans. Brit Mycol. Soc. 78: 366–366, 1982) may also be synonymous with *S. thermophilum*. Members of the complex are known to be producers of thermostable cellulase and β-glucosidase enzymes (Rao and Murthy, Ind. J. Biochem. Biophys. 25: 687–694, 1988; Hayashida and Yoshioka, Agric. Biol. Chem. 44: 1721–1728, 1980). However, there have been no previous reports of the production of a laccase by Scytalidium, or any of the noted synonymous species. It has now been determined that not only does Scytalidium produce a laccase, but the gene encoding this laccase can be used to produce large yields of the enzyme in convenient host systems such as Aspergillus.

Figure 3:
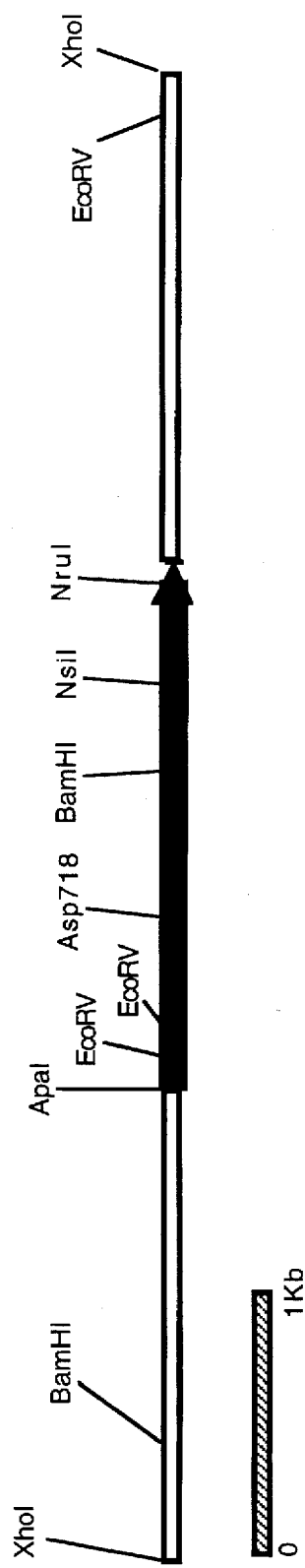
FIG. 3 illustrates the restriction map of a XhoI insert in pShTh6 which contains the S. thermophilum laccase(lccS) gene. The approximate position of the lccS coding region is indicated by a solid black line.

To identify the presence of a laccase gene in Scytalidium, a 5' portion of the *Neurospora crassa* laccase gene(lccl) is used as a probe, under conditions of mild stringency, in southern hybridization of total genomic DNA of different fungal species. An approximately 3 kb laccase specific sequence is detected in the Scytalidium DNA. The *N. crassa* fragment is then used to screen about 12,000 plaques of an *S. thermophilum* genomic DNA library in a λ EMBL4 bacteriophage cloning vector. Nine plaques strongly hybridize with the probe; from these nine, DNA is isolated from four. Each of these clones contains a 3kb BamHI fragment corresponding to the one initially identified in the southern blot of genomic DNA. One of the fragments is subcloned into a pBluescript vector; however, DNA sequencing shows only a portion of the gene to be on this fragment. A 6kb fragment XhoI fragment from the same phage contains the whole lccS gene, and this is then subcloned into pBluescript to derive plasmid pShTh6. A restriction map of the 6 kb insert is shown in FIG. 3.

Once the sequence is determined, the positions of introns and exons within the gene is assigned based on alignment of the deduced amino acid sequence to the corresponding *N. crassa* laccase gene product. From this comparison, it appears that the gene (lccS) of *S. thermophilum* is composed of seven exons(243, 91, 70, 1054 and 390 nucleotides) punctuated by four small introns (63, 58, 55 and 65 nucleotides). The coding region, excluding intervening sequences is very GC-rich(60.8% G+C) and encodes a preproenzyme of 616 amino acids: a 21 amino acid signal peptide and a 24 amino acid propeptide. The sequence of the *S. thermophilum* gene and the predicted amino acid sequence is shown in FIG. 1 (SEQ ID NOS: 1 and 2)

The laccase gene is then used to create an expression vector for transformation of Aspergillus host cells. The vector, pShTh15 contains the *A. oryzae* TAKA-amylase promoter and the *A. niger* glaA terminator regions. The construction of pShTh15 is outlined in FIG. 2. Aspergillus cells are cotransformed with the expression vector and a plasmid containing the pyrG or amdS selectable marker. Transformants are selected on the appropriate selective medium containing ABTS. Laccase-producing colonies exhibit a green halo and are readily isolatable. Selected transformants are grown up in shake flasks and culture broths tested for laccase activity by the syringaldazine method. Shake flask cultures are capable of producing 50 or more mg/liter of laccase, and in fermentors, yields of over 1.6 g/liter are observed.

According to the invention, a Scytalidium gene encoding a laccase can be obtained by methods described above, or any alternative methods known in the art, using the information provided herein. The gene can be expressed, in active form, using an expression vector. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene or various activator genes. To permit the secretion of the expressed protein, nucleotides encoding a signal sequence may be inserted prior to the coding sequence of the gene. For expression under the direction of control sequences, a laccase gene to be used according to the invention is operably linked to the control sequences in the proper reading frame. Promoter sequences that can be incorporated into plasmid vectors, and which can direct the transcription of the laccase gene, include but are not limited to the prokaryotic β-lactamase promoter (Villa-Kamaroff, et al., 1978, Proc. Natl. Acad. Sci. U.S.A. 75:3727–3731) and the tac promoter (DeBoer, et al., 1983, Proc. Natl. Acad. Sci. U.S.A. 80:21–25). Further references can also be found in "Useful proteins from recombinant bacteria" in Scientific American, 1980, 242:74–94; and in Sambrook et al., Molecular Cloning, 1989.

The expression vector carrying the DNA construct of the invention may be any vector which may conveniently be subjected to recombinant DNA procedures, and the choice of vector will typically depend on the host cell into which it is to be introduced. Thus, the vector may be an autonomously replicating vector, i.e. a vector which exists as an extrachromosomal entity, the replication of which is independent of chromosomal replication, e.g. a plasmid, or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA construct of the invention, especially in a bacterial host, are the promoter of the lac operon of *E.coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), or the promoters of the *Bacillus subtilis* xylA and xylB genes. In a yeast host, a useful promoter is the eno-1 promoter. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (glaA), *Rhizomucor miehei* lipase, *A. oryzae* alkaline protease, *A. oryzae* triose phosphate isomerase or *A. nidulans* acetamidase. Preferred are the TAKA-amylase and glaA promoters.

The expression vector of the invention may also comprise a suitable transcription terminator and, in eukaryotes, polyadenylation sequences operably connected to the DNA sequence encoding the laccase of the invention. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B.subtilis* or *B.licheniformis*, or one which confers antibiotic resistance such as ampicillin, kanamycin, chloramphenicol or tetracycline resistance. Examples of Aspergillus selection markers include amds, pyrG, argB, niad, sC, and hygB a marker giving rise to hygromycin resistance. Preferred for use in an Aspergillus host cell are the amds and pyrG markers of *A. nidulans* or *A. oryzae*. A frequently used mammalian marker is the dihydrofolate reductase (DHFR) gene. Furthermore, selection may be accomplished by co-transformation, e.g. as described in WO 91/17243.

It is generally preferred that the expression gives rise to a product that is extracellular. The laccases of the present invention may thus comprise a preregion permitting secretion of the expressed protein into the culture medium. If desirable, this preregion may be native to the laccase of the invention or substituted with a different preregion or signal sequence, conveniently accomplished by substitution of the DNA sequences encoding the respective preregions. For example, the preregion may be derived from a glucoamylase or an amylase gene from an Aspergillus species, an amylase gene from a Bacillus species, a lipase or proteinase gene from *Rhizomucor miehei*, the gene for the α-factor from *Saccharomyces cerevisiae* or the calf preprochymosin gene. Particularly preferred, when the host is a fungal cell, is the preregion for *A. oryzae* TAKA amylase, *A. niger* neutral amylase, the maltogenic amylase form Bacillus NCIB 11837, *B. stearothermophilus* α-amylase, or *Bacillus licheniformis* subtilisin. An effective signal sequence is the *A. oryzae* TAKA amylase signal, the *Rhizomucor miehei* aspartic proteinase signal and the *Rhizomucor miehei* lipase signal.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. Molecular Cloning, 1989).

The cell of the invention either comprising a DNA construct or an expression vector of the invention as defined above is advantageously used as a host cell in the recombinant production of a enzyme of the invention. The cell may be transformed with the DNA construct of the invention, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The host cell may be selected from prokaryotic cells, such as bacterial cells. Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus*, or gram negative bacteria such as *E.coli*. The transformation of the bacteria may for instance be effected by protoplast transformation or by using competent cells in a manner known per se.

The host cell may also be a eukaryote, such as mammalian cells, insect cells, plant cells or preferably fungal cells, including yeast and filamentous fungi. For example, useful mammalian cells include CHO or COS cells. A yeast host cell may be selected from a species of Saccharomyces or Schizosaccharomyces, e.g. *Saccharomyces cerevisiae*. Useful filamentous fungi may selected from a species of Aspergillus, e.g. *Aspergillus oryzae* or *Aspergillus niger*. Alternatively, a strain of a Fusarium species, e.g. *F. oxysporum*, can be used as a host cell. Fungal cells may be transformed by a process involving protoplast formation and transformation of the protoplasts followed by regeneration of the cell wall in a manner known per se. A suitable procedure for transformation of Aspergillus host cells is described in EP 238 023. A suitable method of transforming Fusarium species is described by Malardier et al., 1989.

The present invention thus provides a method of producing a recombinant laccase of the invention, which method comprises cultivating a host cell as described above under conditions conducive to the production of the enzyme and recovering the enzyme from the cells and/or culture medium. The medium used to cultivate the cells may be any conventional medium suitable for growing the host cell in question and obtaining expression of the laccase of the invention. Suitable media are available from commercial suppliers or may be prepared according to published formulae (e.g. in catalogues of the American Type Culture Collection).

The resulting enzyme may be recovered from the medium by conventional procedures including separating the cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, gel filtration chromatography, affinity chromatography, or the like. Preferably, the isolated protein is about 90% pure as determined by SDS-PAGE, purity being most important in food, juice or detergent applications.

In a particularly preferred embodiment, the expression of laccase is achieved in a fungal host cell, such as Aspergillus. As described in detail in the following examples, the laccase gene is ligated into a plasmid containing the *Aspergillus oryzae* TAKA (α-amylase promoter, and the *Aspergillus nidulans* amds selectable marker. Alternatively, the amds may be on a separate plasmid and used in co-transformation. The plasmid (or plasmids) is used to transform an Aspergillus species host cell, such as *A. oryzae* or *A. niger* in accordance with methods described in Yelton et al. (PNAS USA 81: 1470–1474, 1984).

Those skilled in the art will recognize that the invention is not limited to use of the nucleic acid fragments specifically disclosed herein, for example, in FIG. 1. It will also be apparent that the invention encompasses those nucleotide sequences that encode the same amino acid sequences as depicted in FIG. 1, but which differ from those specifically depicted nucleotide sequences by virtue of the degeneracy of the genetic code. Also, reference to FIG. 1, in the specification and the claims will be understood to encompass both the genomic sequence depicted therein as well as the corresponding cDNA and RNA sequences, and the phrases "DNA construct" and "nucleic acid sequences" as used herein will be understood to encompass all such variations. "DNA construct" shall generally be understood to mean a DNA molecule, either single- or double-stranded, which may be isolated in partial form from a naturally occurring gene or which has been modified to contain segments of DNA which are combined and juxtaposed in a manner which would not otherwise exist in nature.

In addition, the invention also encompasses other Scytalidium laccases, including alternate forms of laccase which may be found in *S. thermophilum* and as well as laccases which may be found in other fungi which are synonyms or fall within the definition of *Scytalidium thermophilum* as defined by Straatsma and Samson, 1993, supra. These include *S. indonesiacum, Torula thermophila, Humicola brevis* var. thermoidea, *Humicola brevispora, H. grisea* var. thermoidea, *Humicola insolens*, and *Humicola lanuginosa* (also known as *Thermomyces lanuginosus*). The invention also provides the means for isolation of laccase genes from other species of Scytalidium, such as *S. acidophilum, S. album, S. aurantiacum, S. circinatum, S. flaveobrunneum, S. hyalinum, S. lignicola*, and *S. uredinicolum*. Identification and isolation of laccase genes from sources other than those specifically exemplified herein can be achieved by utilization of the methodology described in the present examples, with publicly available Scytalidium strains. Alternately, the sequence disclosed herein can be used to design primers and/or probes useful in isolating laccase genes by standard PCR or southern hybridization techniques, using the same publicly available strains. Examples of such publicly available strains include, from the American Type Culture Collection, ATCC 16463, 28085, 36346, 48409, 66938 (*S. thermophilum*); 24569 (*S. acidophilum*); 16675 (*S. album*); 22477 (*S. aurantiacum*); 66463 (*S. circinatum*); 13212 (*S. flavo-brunneum*); 52297 (*S. fulvum*); 38906 (*S. hyalinum*); 46858 (*S. indonesiacum*); 18984 (*S. indonesiacum*); 32382 (*S. uredinaolum*); from the International Mycological Institute (IMI; United Kingdom), IMI 243 118 (*S. thermophilum*); from Centraalbureau voor Schimmelcultures (CBS; Netherlands) CBS 183.81, 671.88 (*S. thermophilum*) 367.72 (*S. acidophilum*); 372.65 (*S. album*); 374.65 (*S. aurantiacum*); 654.89 (*S. circinatum*); 244.59 (*S. flavo-brunneum*); 145.78 (*S. hyalinum*); 259.81 (*S. indonesiacum*); 233.57 (*S. lignicola*); 171.40 (*S. terminale*); 616.84 (*S. muscorum*); from Deutsche Sammlung von Mikroorganismenn und Zellkulturen (DSM; Germany) DSM 2842 (*S thermophilum*); DSM 2695 (*S. lignicola*). The invention also encompasses any variant nucleotide sequence, and the protein encoded thereby, which protein retains at least about an 80%, preferably about 85%, and most preferably at least about 90–95% homology with the amino acid sequence depicted in FIG. 1, and which qualitatively retains the laccase activity of the sequence described herein. Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln. It will be apparent to the skilled artisan that such substitutions can be made outside the regions critical to the function of the molecule and still result in an active enzyme. Retention of the desired activity can readily be determined by conducting a standard ABTS oxidation method, such as is described in the present examples.

The protein can be used in number of different industrial processes. These processes include polymerization of lignin, both Kraft and lignosulfates, in solution, in order to produce a lignin with a higher molecular weight. A neutral/alkaline laccase is a particular advantage in that Kraft lignin is more soluble at higher pHs. Such methods are described in, for example, Jin et al., Holzforschung 45(6): 467–468, 1991; U.S. Pat. No. 4,432,921; EP 0 275 544; PCT/DK93/00217, 1992. Laccase is also useful in the copolymerization of lignin with low molecular weight compounds, such as is described in Appl. Microbiol. Biotechnol. 40: 760–767.

The laccase of the present invention can also be used for in-situ depolymerization of lignin in Kraft pulp, thereby producing a pulp with lower lignin content. This use of laccase is an improvement over the current use of chlorine for depolymerization of lignin, which leads to the production of chlorinated aromatic compounds, which are an environmentally undesirable by-product of paper mills. Such uses are described in, for example, Current opinion in Biotechnology 3: 261–266, 1992; J. Biotechnol. 25: 333–339, 1992; Hiroi et al., Svensk papperstidning 5: 162–166, 1976. Since the environment in a paper mill is typically alkaline, the present laccase is more useful for this purpose than other known laccases, which function best under acidic conditions.

Oxidation of dyes or dye precursors and other chromophoric compounds leads to decolorization of the compounds. Laccase can be used for this purpose, which can be particularly advantageous in a situation in which a dye transfer between fabrics is undesirable, e.g., in the textile industry and in the detergent industry. Methods for dye transfer inhibition and dye oxidation can be found in WO 92/01406; WO 92/18683; EP 0495836; Calvo, Mededelingen van de Faculteit Landbouw-wetenschappen/ Rijiksuniversitet Gent. 56: 1565–1567, 1991; Tsujino et al., J. Soc. Chem. 42: 273–282, 1991.

The present laccase can also be used for the polymerization or oxidation of phenolic compounds present in liquids. An example of such utility is the treatment of juices, such as apple juice, so that the laccase will accelerate a precipitation of the phenolic compounds present in the juice, thereby producing a more stable juice. Such applications have been described in Stutz, Fruit processing 7/93, 248–252, 1993; Maier et al., Dt. Lebensmittel-rindschau 86(5): 137–142, 1990; Dietrich et al., Fluss. Obst 57(2): 67–73, 1990.

Laccases such as the Scytalidium laccase are also useful in soil detoxification (Nannipieri et al., J. Environ. Qual. 20: 510–517, 1991; Dec and Bollag, Arch. Environ. Contam. Toxicol. 19: 543–550, 1990).

The invention is further illustrated by the following non-limiting examples.

EXAMPLES

I. ISOLATION OF SCYTALIDIUM THERMOPHILUM LACCASE GENE

A. MATERIALS AND METHODS

1. DNA Extraction and Hybridization Analysis

Total cellular DNA is extracted from fungal cells of *Scytalidium thermophila* strain E421 grown 24 hours in 25 ml of YEG medium (0.5% yeast extract, 2% glucose) using the following protocol: mycelia are collected by filtration through Miracloth (Calbiochem) and washed once with 25 ml of TE buffer. Excess buffer is drained from the mycelia which are subsequently frozen in liquid nitrogen. Frozen mycelia are ground to a fine powder in an electric coffee grinder, and the powder added to 20 ml of TE buffer and 5 ml of 20% SDS (w/v) in a disposable plastic centrifuge tube.

The mixture is gently inverted several times to ensure mixing, and extracted twice with an equal volume of phenol:chloroform:isoamyl alcohol (25:24:1). Sodium acetate (3M solution) is added to give a final concentration of 0.3M and the nucleic acids are precipitated with 2.5 volumes of ice cold ethanol. The tubes are centrifuged at 15,000×g for 30 minutes and the pellet is allowed to air-dry for 30 minutes before resuspending in 0.5 ml of TE buffer. DNase-free ribonuclease A is added to a concentration of 100 µg/ml and the mixture is incubated at 37° C. for 30 minutes. Proteinase K (200 µg/ml) is added and each tube is incubated an additional one hour at 37° C. Finally, each sample is extracted twice with phenol:chloroform:isoamyl alcohol before precipitating the DNA with sodium acetate and ethanol. DNA pellets are dried under vacuum, resuspended in TE buffer, and stored at 4° C.

Total cellular DNA samples are analyzed by Southern hybridization. Approximately 5 µg of DNA is digested with EcoRI and fractionated by size on a 1% agarose gel. The gel is photographed under short wavelength UV and soaked for 15 minutes in 0.5M NaOH, 1.5M NaCl followed by 15 minutes in 1M Tris-HCl, pH 8, 1.5M NaCl. DNA in the gel is transferred onto Zeta-Probe™ hybridization membrane (BioRad Laboratories) by capillary blotting in 20× SSPE (R. W. Davis et al., Advanced Bacterial Genetics, A Manual for Genetic Engineering. Cold Spring Harbor Press. 1980) Membranes are baked for 2 hours at 80° C. under vacuum and soaked for 2 hours in the following hybridization buffer at 45° C. with gentle agitation: 5× SSPE, 35% formamide (v/v), 0.3% SCS, 200 µg/ml denatured and sheared salmon testes DNA. The laccase-specific probe fragment (approx. 1.5 kb) encoding the 5'-portion of the N. crassa lcc1 gene is amplified from N. crassa genomic DNA using standard PCR conditions (Perkin-Elmer Cetus, Emeryville, Calif.) with the following pair of primers: forward primer, 5' CGAGACT-GATAACTGGCTTGG 3' (SEQ ID NO:3); reverse primer, 5' ACGGCGCATTGTCAGGGAAGT 3' (SEQ ID NO:4). The amplified DNA segment is first cloned into a TA-cloning vector (Invitrogen, Inc., San Diego, Calif.), then purified by agarose gel electrophoresis following digestion with EcoRI. The purified probe fragment is radiolabeled by nick translation with $\alpha[^{32}P]dCTP$(Amersham) and added to the hybridization buffer at an activity of approximately $1 \times 10^6$ cpm per ml of buffer. The mixture is incubated overnight at 45° C. in a shaking water bath. Following incubation, the membranes are washed once in 0.2×SSPE with 0.1% SDS at 45° C. followed by two washes in 0.2×SSPE(no SDS) at the same temperature. The membranes are allowed to dry on paper towels for 15 minutes, then wrapped in Saran Wrap™ and exposed to x-ray film overnight at −70° C. with intensifying screens(Kodak).

2. DNA Libraries and Identification of Laccase Clones

Genomic DNA libraries are constructed in the bacteriophage cloning vector λ-EMBL4 (J. A. Sorge, in Vectors, A Survey of Molecular Cloning Vectors and Their Uses, Rodriguez et al., eds, pp.43–60, Butterworths, Boston, 1988). Briefly, total cellular DNA is partially digested with Sau3A and size-fractionated on low-melting point agarose gels. DNA fragments migrating between 9 kb and 23 kb are excised and eluted from the gel using β-agarase (New England Biolabs, Beverly Mass.). The eluted DNA fragments are ligated with BamHI-cleaved and dephosphorylated λ-EMBL4 vector arms, and the ligation mixtures are packaged using commercial packaging extracts (Stratagene, LaJolla, Calif.). The packaged DNA libraries are plated and amplified on *Escherichia coli* K802 cells. Approximately 10,000–20,000 plaques from each library are screened by plaque-hybridization with the radiolabeled lcc1 DNA fragment using the conditions described above. Plaques which give hybridization signals with the probe are purified twice on *E. coli* K802 cells, and DNA from the corresponding phage is purified from high titer lysates using a Qiagen Lambda kit (Qiagen, Inc., Chatsworth, Calif.).

3. Analysis of Laccase Genes

Restriction mapping of laccase clones is done using standard methods (Lewin, Genes. 2d ed., Wiley & Sons, 1985, New York). DNA sequencing is done with an Applied Biosystems Model 373A automated DNA Sequencer (Applied Biosystems, Inc., Foster City, Calif.) using the primer walking technique with dye-terminator chemistry (H. Giesecke et al., J. Virol. Methods 38: 47–60, 1992). oligonucleotide sequencing primers are synthesized on an Applied Biosystems model 394 DNA/RNA Synthesizer.

B. RESULTS AND DISCUSSION

1. Identification of Laccase Gene Sequence

Total cellular DNA samples are prepared from the species *Neurospora crassa, Botrytis cinerea,* and Scytalidium. Aliquots of these DNA preparations are digested with BamHI and fractionated by agarose gel electrophoresis. DNA in the gel is blotted to a Zeta-Probe™ membrane filter (BioRad Laboratories, Hercules, Calif.) and probed under conditions of mild stringency with a radiolabeled fragment encoding a portion of the *N. crassa* lcc1 gene, as described above. Laccase-specific sequences are detected in the genomes of *S. thermophilum* and the *N. crassa* control, but not in the *B. cinerea* genomic DNA with this probe.

2. Cloning and Characterization of *Scytalidium thermophila* Laccase (StL) Gene

The *S. thermophilum* laccase gene is isolated using plaque hybridization to screen the genomic DNA library made in λ-EMBL4. The library contains approximately 250,000 independent clones before amplification, and 12,000 plaques are screened by hybridization with a radiolabeled *N. crassa* laccase gene fragment as described above. Nine plaques are identified which hybridize strongly to the probe. DNA is isolated from four of these clones and analyzed by restriction mapping. All four contain a 3kb BamHI fragment that is originally identified in southern blotting with genomic DNA as described above. This fragment is isolated from one clone and inserted into a pBluescript vector(Stratagene Cloning Systems, La Jolla, Calif.). However, DNA sequence analysis indicates that only a portion of the gene is located on this segment. Consequently, a 6 kb XhoI fragment which contains the entire lccS gene is subcloned into pBluescript to derive the plasmid pShTh6. A restriction map of the 6 kb insert in this plasmid is shown in FIG. 3. The nucleic acid sequence is shown in FIG. 1 and SEQ ID NO: 1. The deduced amino acid sequence of StL is obtained on the basis of amino acid sequence homology with *N. crassa* laccase. StL shares approximately 58% amino acid sequence identity with NcL, and this sequence similarity is highest among those amino residues that are involved in the formation of the active site copper center. StL, like NcL appears to be synthesized as a preproenzyme(616 amino acids with a 21 amino acid signal peptide and a propeptide of 24 amino acids). However, since the amino terminal sequence of the mature StL protein is not yet determined, the exact length of the propeptide is not certain. There are five potential sites for N-linked glycosylation in StL. A potential C-terminal processing signal with homology to *N. crassa* laccase also exists in StL (Asp-Ser-Gly-Leu*$Lys_{564}$ (SEQ ID NO:5)) which may result in the proteolytic removal of the last seven amino acids from the primary translation product.

The presence of four small introns (63, 58, 55 and 65 nucleotides) is determined by comparing the open reading frames within the coding region of lccS to the primary structure of NcL. Excluding these intervening sequences, the coding region contains 60.8% G+C. The base composition of lccS reflects a bias for codons ending in G or C.

II. EXPRESSION OF SCYTALIDIUM LACCASE IN ASPERGILLUS

A. MATERIALS AND METHODS

1. Bacterial and Fungal Host Strains

*Escherichia coli* JM101 (Messing et al., Nucl. Acids Res. 9:309–321, 1981) is used as a host for construction and routine propagation of laccase expression vectors in this study. Fungal hosts for laccase expression included the *Aspergillus niger* strain Bo-1, as well as a uridine-requiring (pyrG) mutant of the α-amylase-deficient *Aspergillus oryzae* strain HowB104.

2. Plasmids

Plasmid pSHTh5 is a pBluescript(Stratagene Cloning Systems, LaJolla, Calif.) derivative which contains a 6 kb XhoI fragment of *S. thermophilum* DNA encoding StL. Plasmid pToC68 (WO 91/17243) contains the *A. oryzae* TAKA-amylase promoter and *A. niger* glaA terminator, and pToC90 (WO 91/17243) carries the *A. nidulans* amdS gene.

3. Construction of Laccase Expression Vectors

Figure 2A:
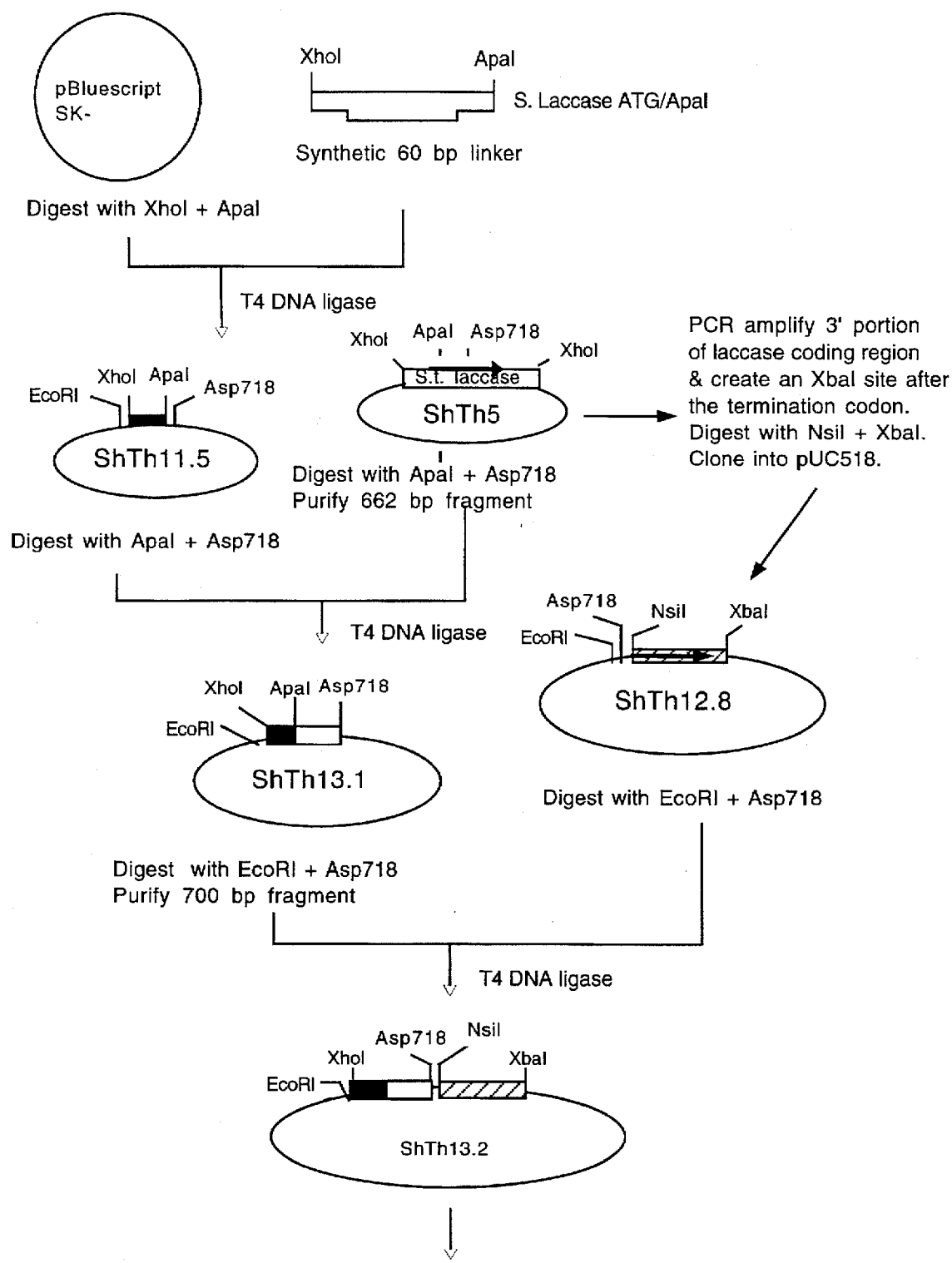
FIG. 2 illustrates the construction of plasmid pShTh15.
Figure 2B:
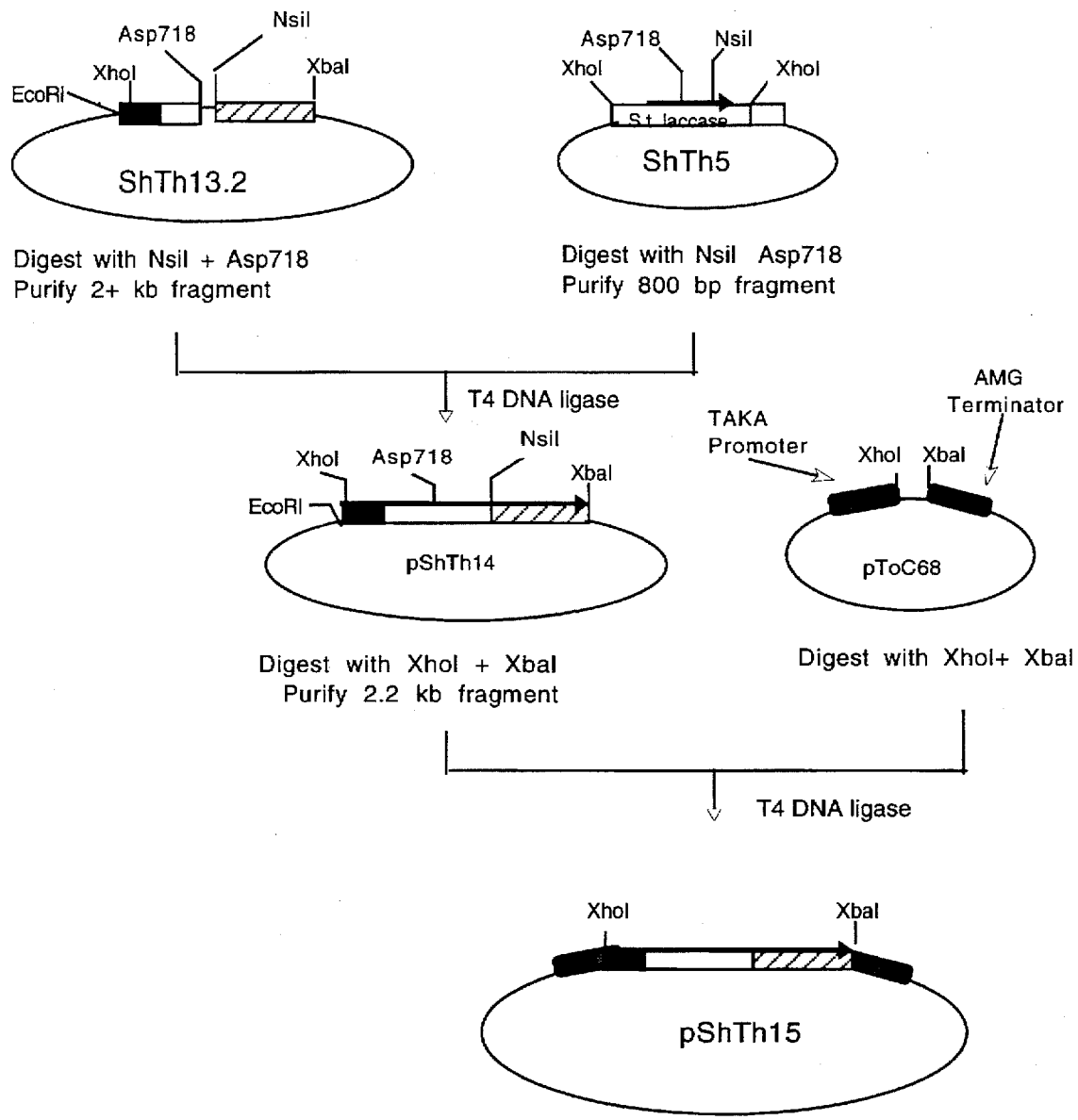

The construction strategy for the laccase expression vector pShTh15 is outlined in FIG. 2. The promoter directing transcription of the laccase gene is obtained from the *A. oxyzae* α-amylase (TAKA-amylase) gene (Christensen et al., supra), and terminator from the *A. niger* glaA (glucoamylase) terminator region. The expression vector is constructed as follows. A 60 basepair synthetic DNA linker, 5' TCGAGATGAAGCGCTTCTTCATTAAT-AGCCTTCTGCTTCTCGCAGGGCTCCT-CAACTCAGGGGCC 3' (SEQ ID NO:6) 3' CTACTTCGCGAAGAAGTAATTATCGGAAGACGAA-GAGCGTCCC- GAGGAGTTGAGTCC 5' (SEQ ID NO:7) including the region from start codon to an ApaI site, is inserted into XhoI- and ApaI-digested pBluescriptSK- (Stratagene, LaJolla, Calif.) to produce an intermediate termed pShTh11.5. This vector is digested with ApaI and Asp718 and ligated with a 662 base pair ApaI-Asp718 fragment encoding a portion of StL from pShTh5, generating a second intermediate called pShTh13.1. An XbaI site is introduced immediately downstream of the stop codon using pShTh5 as a template for a PCR reaction with the following primers:forward: 5'GTCATGAACAATGACCT 3' (SEQ ID NO:8); reverse: 5'AGAGAGTCTAGATTAAACAATC-CGCCCAACTAC3' (SEQ ID NO:9). The amplified fragment is digested with NsiI and XbaI and subcloned into pUC518 to created the intermediate called pShTh12.8. The pShTh12.8 vector is digested with EcoRI and Asp718 and ligated with a 700 base pair EcoRI-Asp718 fragment from pShTh13.1 to generate pShTh13.1 to generate pShTh13.2. An 800 base pair NsiI-Asp718 fragment containing the final portion of the laccase coding region is obtained from pShTh5 and inserted into NsiI- and Asp718-cleaved pShTh13.2 to give pShTh14. Lastly, the 2.2 kb laccase coding region in pShTh14 is removed by cleavage with XhoI and XbaI and inserted between the XhoI and XbaI sites of pToC68 to generate the expression vector pShTh15.

4. Transformation of Aspergillus Host Cells

Methods for co-transformation of Aspergillus strains are as described in Christensen et al., supra. For introduction of the laccase expression vectors into *A. oryzae* HowB 104 pyrG, equal amounts (approximately 5 µg each) of laccase expression vector and pPyrG, which harbors the cloned *A. nidulans* pyrG gene, are used. Protrophic(Pyr$^+$) transformants are selected on Aspergillus minimal medium (Rowlands and Turner, Mol. Gen. Genet. 126: 201–216, 1973), and the transformants are screened for the ability to produce laccase on minimal medium containing 1 mM 2.2'-azinobis(3-ethylbenzthiazolinesulfonic acid)[ABTS]. Cells which secrete active laccase oxidize the ABTS, producing a green halo surrounding the colony. *A. niger* Bo-1 protoplasts are co-transformed using equal amounts (approximately 5 µg each) of laccase expression vector and pToC90 which contains the *A. nidulans* amds (acetamidase) gene (Hynes et al., Mol. Cell Biol. 3: 1430–1439, 1983. AmdS$^+$ transformants are selected on Cove minimal medium (Cove, Biochim. Biophys. Acta 113: 51–56, 1966) with 1% glucose as the carbon source and acetamide as the sole nitrogen source and screened for laccase expression on Cove medium with 1 mM ABTS.

5. Analysis of Laccase-Producing Transformants

Transformants which produce laccase activity on agar plates are purified twice through conidiospores and spore suspensions in sterile 0.01% Tween-80 are made from each. The density of spores in each suspension is estimated spectrophotometrically ($A_{595}$ nm). Approximately 0.5 absorbance units of spores are used to inoculate 25 ml of ASPO4 or MY50 medium in 125 ml plastic flasks. The cultures are incubated at 37° C. with vigorous aeration (approximately 200 rpm) for four to five days. Culture broths are harvested by centrifugation and the amount of laccase activity in the supernatant is determined using syringaldazine as a substrate. Briefly, 800 µl of assay buffer (25 mM sodium acetate, pH 5.5, 40 µM $CuSo_4$) is mixed with 20 µl of culture supernatant and 60 µl of 0.28 mM syringaldazine stock solution (Sigma Chemical Co., St. Louis, Mo.) in 50% ethanol. The absorbance at 530 nm is measured over time in a Genesys 5 UV-vis spectrophotometer (Milton-Roy). One laccase unit(LACU) is defined as the amount of enzyme which oxidizes one µmole of substrate per minute at room temperature. SDS-polyacrylamide gel electrophoresis(PAGE) is done using precast 10–27% gradient gels from Novex(San Diego, Calif.). Protein bands are developed using Coomassie Brilliant Blue(Sigma).

B. RESULTS AND DISCUSSION

1. Expression of Scytalidium Laccase

The expression vector pShTh15 is used in conjunction with pPyrG (*A. nidulans* pyrG) or pToC90 (*A. nidulans* amds) plasmids to generate *A. oryzae* and *A. niger* co-transformants which express StL. As shown in Table 1, the number of laccase-producing co-transformants obtained in *A. oryzae* HowB104pyrG is small (3.7% of Pyr$^+$ transformants) compared to the number obtained in *A. niger* Bo-1 using amds selection (71.5% of AmdS$^+$ transformants). It is unknown whether this is due to an abnormally low co-transformation(i.e., integration) frequency or extremely low expression or laccase degradation in many *A. oryzae* transformants. Expression levels of StL range from about 50 mg/l in shake flasks and 1–2 g/l in a fermentor.

III. PURIFICATION AND CHARACTERIZATION OF RECOMBINANT SCYTALIDIUM LACCASE

A. MATERIALS AND METHODS

1. Materials

Chemicals used as buffers and substrates are commercial products of at least reagent grade. Chromatography is performed on either a Pharmacia FPLC. Spectroscopic assays are conducted on either a spectrophotometer (Shimadzu PC160) or a microplate reader(molecular Devices). Britton & Robinson (B&R) buffers are prepared according to the protocol described in Quelle, Biochemisches Taschenbuch, H. M. Raven, II. Teil, S.93 u. 102, 1964.

2. Fermentation

A 1 ml aliquot of a spore suspension of *Aspergillus oryzae* transformant HowB104-pShTh15-2 (approximately $10^9$ spores/ml) is added aseptically to a 500 ml shake flask containing 100 ml of sterile shake flask medium (maltose, 50 g/l; $MgSO_4.7H_2O$, 2 g/l; $KH_2PO_4$, 10 g/l; $K_2SO_4$, 2 g/l; $CaCl_2.2H_2O$ 0.5 g/l; Citric acid, 2 g/l; yeast extract, 10 g/l; trace metals[$ZnSO_4.7H_2O$, 14.3 g/l; $CuSO_4.5H_2O$, 2.5 g/l; $NiCl_2.6H_2O$, 0.5 g/l; $FeSO_4.7H_2O$, 13.8 g/l, $MnSO_4.H_2O$, 8.5 g/l; citric acid, 3.0 g/l], 0.5 ml/l; urea, 2 g/l, made with tap water and adjusted to pH 6.0 before autoclaving), and incubated at 37° C. on a rotary shaker at 200 rpm for 18 hours. 50 ml of this culture is aseptically transferred to a 3 liter fermentor containing 1.8 liters of the fermentor media ($MgSO_4.7H_2O$, 2 g/l; $KH_2PO_4$, 2 g/l; citric acid 4 g/l; $K_2SO_4$, 3 g/l; $CaCl_2.2H_2O$, 2 g/l; trace metals, 0.5 ml/l; pluronic antifoam, 1 ml/l). The fermentor temperature is maintained at 34° C. by the circulation of cooling water through the fermentor jacket. Sterile air is sparged through the fermentor at a rate of 1.8 liter/min (1 v/v/m). The agitation rate is maintained between 600 and 1300 rpm at approximately the minimum level required to maintain the dissolved oxygen level in the culture above 20%. Sterile feed (Nutriose 725[maltose syrup], 225 g/l; urea, 30 g/l; yeast extract, 15 g/l; pluronic antifoam, 1.5 ml/l, made up with distilled water and autoclaved) is added to the fermentor by use of a peristaltic pump. The feed rate profile during the fermentation is as follows: 30 g of feed is added initially before inoculation; 0–24 h, 2 g/l h; 24–48 h, 4 g/l h; 48 h-end, 6 g/l.

Copper (in the form of $CuCl_2$, CuSO4 or other soluble salt) is made as a 400× stock in water or a suitable buffer, filter sterilized and added aseptically to the tank to a final level of 0.5 mM.

Samples for enzyme activity determination are withdrawn and filtered through Miracloth to remove mycelia. These samples are assayed for laccase activity by the LACU assay described above. Laccase activity is found to increase continuously during the course of the fermentation, with a value of approximately 3.6 LACU/ml achieved after 115 hours in the fermentation containing excess copper. At a specific activity of 1.9 LACU/mg, this corresponds to over 1.8 g/l recombinant laccase expressed by this transformant.

3. Enzymatic Assay

Laccase activity is determined by syringaldazine oxidation at 30° C. in a 1-cm quartz cuvette. 60 µl syringaldazine stock solution (0.28 mM in 50% ethanol) and 20 µl sample are mixed with 0.8 ml preheated buffer solution. The oxidation is monitored at 530 nm over 5 minutes. The activity is expressed as µmole substrate oxidized per minute. B&R buffers with various pHs are used. The activity unit is referred to here as "SOU". A buffer of 25 mM sodium acetate, 40 µM $CuSO_4$, pH 5.5, is also used to determine the activity, which is referred to as LACU, as defined above. 2,2'-azinobis(3-ethylbenzo thiazoline-6-sulfonic acid) (ABTS) oxidation assays are done using 0.4 mM ABTS, B&R buffer, pH 4.1, at room temperature by monitoring $\Delta A_{405}$. An ABTS oxidase activity overlay assay is performed by pouring cooled ABTS-agarose(0.05 g ABTS, 1 g agarose, 50 ml $H_2O$, heated to dissolve agarose) over a native-IEF gel and incubating at room temperature. Thermostability analysis is performed using samples that have ~3 µM enzyme preincubated for one hour in B&R buffer, at pH 2.7, 6.1, and 9.0, and various temperatures. Samples are assayed after a 44-fold dilution into B & R buffer, pH 4.1, at room temperature.

3. Purification from a Fermentor Broth 1.2 liters of cheese-cloth filtered broth (pH 7.9, 13 mS) is filtered through Whatman #2 filter paper and concentrated on a Spiral Concentrator(Amicon) with a S1Y100 membrane (MWCO:100) to 200 ml. The concentrate is adjusted to 0.86 mS by diluting it in water and reconcentrated on S1Y100 to 324 ml. The washed and concentrated broth has a dense greenish color.

The broth is frozen overnight at −20° C., thawed the next day(without any loss of activity) and loaded onto a Q-Sepharose XK26 column (120 ml), preequilibrated with 10 mM Tris, pH 7.7, 0.9 mS. The blue laccase band is eluted during a linear gradient with 2M NaCl.

Pooled laccase fractions(44 ml), dialyzed in 3.5 liters of 10 mM NaAc, pH 5.5, 0.8 mS at 4° C. overnight, are loaded onto a Mono-Q 16/10 (40 ml), preequilibrated with 10 mM MES, pH 5.3, 0.8 mS. The laccase eluted during a linear gradient with 1M NaCl shows apparent homogeneity on SDS-PAGE.

4. Analysis of Amino Acid Content and N-terminus

N-terminal sequencing is performed on an ABI 476A sequencer; and total amino acid analysis, from which the extinction coefficient of laccase is determined, is performed on a HP AminoQuant instrument.

B. RESULTS AND DISCUSSION

1. Purification

From 1200 ml fermentor broth, about 0.6 g of laccase are isolated. Initial concentration using a membrane with MWCO of 100 kDa removes significant amounts of brown material and small contaminant proteins. The low affinity of the laccase toward Q-Sepharose matrix equilibrated with 10 mM Tris, pH 7.7, facilitates its separation from other impurities. The enriched fractions are further purified by Mono-Q at pH 5.3. Although it has a pI of 5.1, the laccase migrates slowly on Mono-Q and is separated from impurities during the washing by 10 mM MES, pH 5.3. An overall 15-fold purification and a recovery of 60% are achieved.

2. Characterization

The purified laccase shows a MW of 75–80 kDa on SDS-PAGE. The difference between the MW derived from DNA sequence(63 kDa) and the observed MW is attributable to glycosylation. Native IEF shows 3 bands near pI of about 5.1, which are active in ABTS overlay assay.

3. N-terminal Sequencing

Directly sequencing the N-terminus of the purified laccase from samples either in desalted solution or on PVDF membrane are unsuccessful. This result suggests a blocked N-terminus, likely a pyroglutamate site based on the gene sequence.

The spectrum of the blue laccase has absorption maxima at 276 and 602 nm; with $AbS_{280}/AbS_{600}=23$ and $Abs_{330}/Abs_{589}=2.1$. The extinction coefficient determined by amino acid analysis is 1.9 l/(g*cm).

The activity is tested by using either syringaldazine or ABTS as substrates. Expressed as per $Abs_{280}$ or per mg, the laccase has a value of 2.2 or 4.2 units for SOU at pH 7, respectively.

Figure 4:
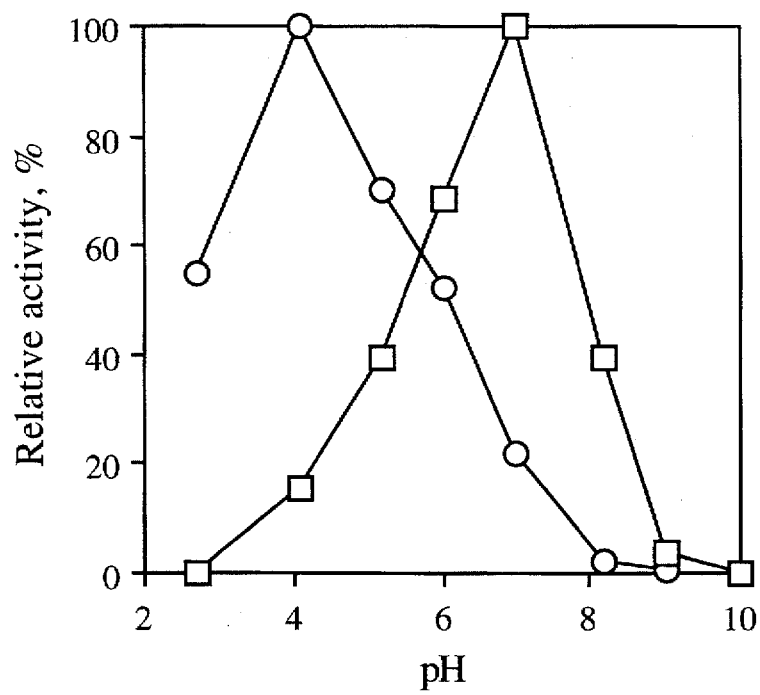
FIG. 4 illustrates the pH profiles of the laccase activity with syringaldazine(squares) and 2,2"azinobis(3-ethylbenzothiazoline-6-sulfonic acid)(circles) as substrate.
Figure 5:
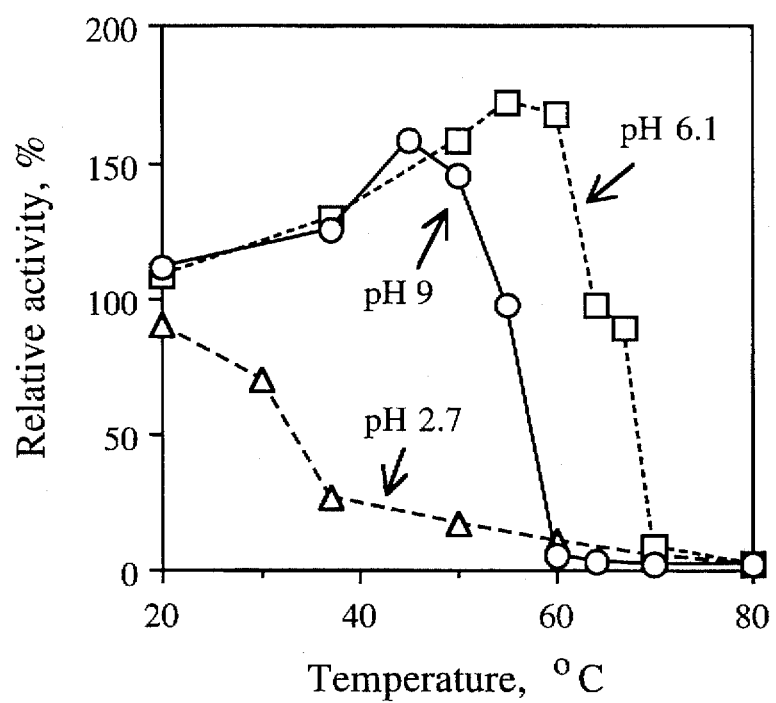
FIG. 5 illustrates the thermostability in B&R buffers of the laccase at pH 2.7, 6.1, and 9.0. Preincubation times are 1 hour. Activities are assayed by ABTS oxidation at 20° C. in B&R buffer, pH 4.1.

The pH profiles of laccase activity has optimal pH of 7 and 4, for syringaldazine and ABTS oxidation, respectively (FIG. 4). Thermostability analysis at three pHs is shown in FIG. 5. The laccase is more stable at neutral to alkaline pH than at acidic pH. Thermoactivation is also observed in neutral-alkaline pH range.

Deposit of Biological Materials

The following biological material has been deposited under the terms of the Budapest Treaty with the Agricultural Research Service Patent Culture Collection, Northern Regional Research Center, 1815 University Street, Peoria, Ill., 61604 and given the following accession number.

| Deposit | Accession Number |
|---|---|
| *E. coli* JM101 containing pShTh15 | NRRL B-21262 |

What we claim is:

1. A DNA construct comprising a nucleic acid sequence encoding a laccase having at least 95% homology with the amino acid sequence of SEQ ID NO:2.

2. A DNA construct comprising a nucleic acid sequence encoding a laccase having an amino acid sequence of SEQ ID NO:2, or its complementary strand.

3. The construct of claim 2, wherein the nucleic acid sequence encodes a laccase having an amino sequence of SEQ ID NO:2.

4. The construct of claim 2, wherein the nucleic acid sequence is set forth in SEQ ID NO:1, or its complementary strand.

5. The construct of claim 4, wherein the nucleic acid sequence is set forth in SEQ ID NO:1.

6. A DNA construct comprising a nucleic acid sequence contained in plasmid pShTh15 which is contained in *Escherichia coli* NRRL B-21262.

7. A recombinant vector comprising a DNA construct of claim 1.

8. The vector of claim 7 in which the sequence is operably linked to a promoter sequence.

9. The vector of claim 8 in which the promoter is a fungal or yeast promoter.

10. The vector of claim 8 in which the promoter is the TAKA amylase promoter of *Aspergillus oryzae*.

11. The vector of claim 8 in which the promoter is the glucoamylase promoter of *Aspergillus niger* or *Aspergillus awamori*.

12. The vector of claim 7 which further comprises a selectable marker.

13. The vector of claim 12 in which the selectable marker is selected from the group consisting of amdS, pyrG, argB, niaD, sC, and hygB.

14. The vector of claim 13 in which the selectable marker is the amdS marker of *Aspergillus nidulans* or *Aspergillus oryzae*, or the pyrG marker of *Aspergillus nidulans*, *Aspergillus niger*, *Aspergillus awamori*, or *Aspergillus oryzae*.

15. The vector of claim 14 which comprises the TAKA amylase promoter of *Aspergillus oryzae* and the amdS or pyrG marker of *Aspergillus nidulans* or *Aspergillus oryzae*.

16. A recombinant host cell comprising a DNA construct of claim 1.

17. The host cell of claim 16 which is a fungal cell.

18. The host cell of claim 17 which is an Aspergillus cell.

19. The host cell of claim 16 in which the construct is integrated into the host cell genome.

20. The host cell of claim 19 in which the construct is contained on a vector.

21. The host cell of claim 16 which comprises a construct containing a sequence encoding the amino acid sequence depicted in SEQ ID NO.2.

22. A method for producing a laccase, comprising
 (a) culturing a host cell of claim 16 under conditions conducive to expression of the laccase; and
 (b) recovering the laccase from the culture.

23. A method for producing a laccase, comprising
 (a) culturing a host cell of claim 21 under conditions conducive to expression of the laccase; and
 (b) recovering the laccase from the culture.

* * * * *